(12) United States Patent
Bost et al.

(10) Patent No.: US 11,517,445 B2
(45) Date of Patent: Dec. 6, 2022

(54) SPINAL IMPLANTS CONFIGURED FOR TISSUE SPARING ANGLE OF INSERTION AND RELATED METHODS

(71) Applicant: CENTINEL SPINE, LLC, New York, NY (US)

(72) Inventors: Stephanie M. Bost, West Chester, PA (US); Andrew J. McQuaide, Lincoln University, PA (US); John Parry, West Chester, PA (US)

(73) Assignee: CENTINEL SPINE, LLC, New York, NY (US)

( * ) Notice: Subject to any disclaimer, the term of this patent is extended or adjusted under 35 U.S.C. 154(b) by 418 days.

(21) Appl. No.: 16/851,710

(22) Filed: Apr. 17, 2020

(65) Prior Publication Data
US 2020/0261242 A1 Aug. 20, 2020

Related U.S. Application Data

(62) Division of application No. 15/094,868, filed on Apr. 8, 2016, now Pat. No. 10,624,757.
(Continued)

(51) Int. Cl.
*A61F 2/44* (2006.01)
*A61F 2/30* (2006.01)

(52) U.S. Cl.
CPC ........ *A61F 2/4455* (2013.01); *A61F 2/30771* (2013.01); *A61F 2002/3008* (2013.01);
(Continued)

(58) Field of Classification Search
None
See application file for complete search history.

(56) References Cited

U.S. PATENT DOCUMENTS 5,865,845 A 2/1999 Thalgott
6,274,770 B1 6/2001 Michelson
(Continued)

FOREIGN PATENT DOCUMENTS

FR 2703580 A1 10/1994
GB 2457673 A 8/2009
(Continued)

OTHER PUBLICATIONS

Shane Thomas (Authorized Officer), International Search Report and Written Opinion dated Jul. 7, 2016, PCT Application No. PCT/US2016/026806, filed Apr. 8, 2016, pp. 1-11.
(Continued)

*Primary Examiner* — Sameh R Boles
(74) *Attorney, Agent, or Firm* — Farber LLC

(57) ABSTRACT

Spinal implants that are configured for a minimally invasive approach to a patient's intervertebral disc space, optimized to avoid blood vessels and nervous tissue, maximizing endplate coverage and promoting sagittal balance, are provided. Insertion and fixation can be accomplished through a narrow access window, thereby allowing better access to more spinal levels while being less invasive than other approaches. The spinal implants may facilitate fusion, and include visualization features to assist in the implantation and verify proper placement and vary segmental angle of lordosis. Methods of implanting the spinal implants to treat a patient's spine are also disclosed.

19 Claims, 10 Drawing Sheets

US 11,517,445 B2
Page 2

Related U.S. Application Data

(60) Provisional application No. 62/145,161, filed on Apr. 9, 2015.

(52) U.S. Cl.
CPC .............. *A61F 2002/3082* (2013.01); *A61F 2002/30266* (2013.01); *A61F 2002/30784* (2013.01)

(56) References Cited

U.S. PATENT DOCUMENTS

| | | |
|---|---|---|
| 6,258,125 B1 | 7/2001 | Paul et al. |
| 6,454,805 B1 | 9/2002 | Baccelli et al. |
| 6,482,233 B1 | 11/2002 | Aebi et al. |
| 6,613,090 B2 | 9/2003 | Fuss et al. |
| 6,984,245 B2 | 1/2006 | McGahan et al. |
| 7,083,625 B2 | 8/2006 | Berry |
| 7,137,997 B2 | 11/2006 | Paul |
| 7,156,875 B2 | 1/2007 | Michelson |
| 7,387,643 B2 | 6/2008 | Michelson |
| 7,462,195 B1 | 12/2008 | Michelson |
| 7,635,371 B2 | 12/2009 | McGahan et al. |
| 7,749,269 B2 | 7/2010 | Peterman et al. |
| 7,763,078 B2 | 7/2010 | Peterman et al. |
| 7,776,095 B2 | 8/2010 | Peterman et al. |
| 7,811,325 B2 | 10/2010 | Cannon et al. |
| D629,108 S | 12/2010 | Richter et al. |
| 7,988,734 B2 | 8/2011 | Peterman et al. |
| 8,092,537 B2 | 1/2012 | Mcgahan et al. |
| 8,206,397 B2 | 6/2012 | Mcgahan et al. |
| D664,252 S | 7/2012 | Weiland et al. |
| 8,323,340 B2 | 12/2012 | Michelson |
| 8,425,610 B2 | 4/2013 | Guyer et al. |
| 8,512,409 B1 | 8/2013 | Mertens et al. |
| 8,529,627 B2 | 9/2013 | Baynham |
| 8,597,359 B2 | 12/2013 | Butler et al. |
| 8,673,005 B1 | 3/2014 | Pimental et al. |
| 8,690,926 B2 | 4/2014 | Thibodeau |
| 8,690,928 B1 | 4/2014 | Walkenhorst et al. |
| 8,715,366 B2 | 5/2014 | Borden |
| 8,734,521 B2 | 5/2014 | Freeman et al. |
| 8,740,983 B1 | 6/2014 | Arnold et al. |
| 8,834,569 B2 | 9/2014 | Michelson |
| 8,840,668 B1 | 9/2014 | Donahoe et al. |
| 8,900,309 B2 | 12/2014 | James et al. |
| 2005/0010292 A1 | 1/2005 | Carrasco |
| 2005/0119753 A1 | 6/2005 | McGahan et al. |
| 2007/0073400 A1 | 3/2007 | Paul |
| 2008/0234828 A1 | 9/2008 | Wagner et al. |
| 2008/0249622 A1 | 10/2008 | Gray |
| 2008/0281425 A1 | 11/2008 | Thalgott et al. |
| 2009/0093883 A1 | 4/2009 | Carrasco |
| 2010/0204798 A1 | 8/2010 | Gerbec et al. |
| 2011/0230970 A1 | 9/2011 | Lynn, Jr. et al. |
| 2011/0295372 A1 | 12/2011 | Peterman et al. |
| 2012/0010717 A1 | 1/2012 | Spann |
| 2012/0158143 A1 | 6/2012 | Shapiro |
| 2012/0292814 A1 | 11/2012 | Spratt et al. |
| 2013/0158667 A1 | 6/2013 | Tabor et al. |
| 2013/0245763 A1 | 9/2013 | Mauldin |
| 2014/0142708 A1 | 5/2014 | Peterman et al. |
| 2014/0156008 A1 | 6/2014 | Flickinger et al. |
| 2014/0163570 A1 | 6/2014 | Reynolds et al. |
| 2014/0180423 A1 | 6/2014 | Pimenta et al. |
| 2014/0277489 A1 | 9/2014 | Davenport et al. |
| 2014/0277497 A1* | 9/2014 | Bennett ............... A61F 2/4455 623/17.16 |
| 2014/0309742 A1 | 10/2014 | Curran et al. |
| 2015/0051705 A1 | 2/2015 | James et al. |

FOREIGN PATENT DOCUMENTS

| | | |
|---|---|---|
| WO | 01/62191 A2 | 8/2001 |
| WO | 2014/125428 A1 | 8/2014 |
| WO | 2014/151175 A1 | 9/2014 |

OTHER PUBLICATIONS

Extended European Search Report for corresponding EP Appl. No. 16 777 435.5 dated Oct. 25, 2018.

* cited by examiner

SPINAL IMPLANTS CONFIGURED FOR TISSUE SPARING ANGLE OF INSERTION AND RELATED METHODS

CROSS-REFERENCE TO RELATED APPLICATIONS

This application is a divisional of U.S. patent application Ser. No. 15/094,868, filed on Apr. 8, 2016, which claims benefit of U.S. Provisional Application No. 62/145,161, filed on Apr. 9, 2015, and entitled "SPINAL IMPLANT CONFIGURED FOR OBLIQUE ANGLE INSERTION AND RELATED METHODS," the entire contents of which are incorporated herein by reference.

TECHNICAL FIELD

The present disclosure relates to orthopedic implants, and more particularly, to minimally invasive spinal implants that facilitate fusion of bone segments and associated methods. Even more particularly, the disclosure relates to spinal fusion implants configured for insertion along an oblique angular trajectory into the lumbar spine, and related methods.

BACKGROUND

The integrity of the spine and its subcomponents like the vertebral bodies and intervertebral discs, both of which are well known structural body parts that make up the spine, is a key factor to maintaining a patient's good health. These parts may become weakened, damaged or broken as a result of trauma, injury, or disease (e.g., by tumor, autoimmune disease), or as a result of wear over time, or degeneration caused by the normal aging process.

In many instances, one or more damaged structural body parts can be repaired or replaced with a prosthesis or implant. For example, specific to the spine, one known method of repair is to remove the damaged vertebra (in whole or in part) and/or the damaged disc (in whole or in part) and replace it with an implant or prosthesis. In some cases, it is necessary to stabilize a weakened or damaged spinal region by reducing or inhibiting mobility in the area to avoid further progression of the damage and/or to reduce or alleviate pain caused by the damage or injury. In other cases, it is desirable to join together the damaged vertebrae and/or induce healing of the vertebrae. Accordingly, an implant or prosthesis for rigid fixation of the vertebrae may be utilized to facilitate fusion between two adjacent vertebrae. The implant or prosthesis may be implanted without attachment means, or fastened in position between adjacent structural body parts (e.g., adjacent vertebral bodies).

Typically, an implant or prosthesis is secured directly to a bone structure by mechanical or biological means. One manner of spine repair involves attaching a fusion implant or prosthesis to adjacent vertebral bodies using a fixation element, such as a bone screw. Most implants and their attachment means are configured to provide an immediate, rigid fixation of the implant to the implantation site. Unfortunately, after implantation the implants tend to subside, or settle, into the surrounding environment as the patient's weight is exerted upon the implant. In some cases, this subsidence may cause the rigidly fixed attachment means to either loosen, dislodge or potentially damage one or more of the vertebral bodies.

Several known surgical techniques can be used to implant a spinal prosthesis. The suitability of any particular technique may depend upon the amount of surgical access available at the implant site. For instance, a surgeon may elect a particular entry pathway depending on the size of the patient or the condition of the patient's spine, such as where a tumor, scar tissue, great vessels, or other obstacle is present. Other times, it may be desirable to minimize intrusion into the patient's musculature and associated ligamentous tissue. In some patients who have had prior surgeries, implants or fixation elements may have already been inserted into the patient's spine, and as such, an implant introduction pathway may have to account for these prior existing conditions.

Thus, it is desirable to provide an implant that can be easily inserted using minimally invasive retractor instrumentation in accordance with a specific pathway or approach. This facilitates a segmental or open approach to multiple levels of the spine. For example, in certain situations, it is desirable to provide a spinal implant that can be inserted at an oblique angle into the lumbar spine to avoid damage to the patient, while also being suitable for insertion by way of a minimally invasive approach.

BRIEF SUMMARY

The embodiments provide spinal implants that are configured for a tissue sparing or an oblique angular approach to a patient's intervertebral disc space. The spinal implants may facilitate fusion, and include anti-migration and anti-rotation features as well as visualization features to assist in the implantation and verify proper placement. The implants support a narrow access oblique surgical approach while maximizing endplate coverage and promoting sagittal balance. The oblique approach provides better access to more spinal levels and is potentially less invasive than other approaches including midline and lateral approaches.

In accordance with one exemplary embodiment, a spinal implant is provided having a body with an upper surface, a lower surface, and a pair of sidewalls extending therebetween. The sidewalls may be connected by an intermediate wall segment and converge at a nose or tip. The pair of sidewalls includes one sidewall that is longer than the other sidewall. The body may further include a central opening extending through the upper and lower surfaces, and one or more apertures within the intermediate wall segment for receiving a fixation element. The body may be configured for insertion along a trajectory represented by an axis that is oblique relative to a midline of a vertebral body of a patient's spine. The spinal implant may additionally include anti-migration and/or anti-rotation features as well as visualization markers. The apertures are configured to receive fixation elements, such as bone screws and the like. The fixation element may comprise one or more anti-backout features, such as a split ring. The spinal implant facilitates fusion and may be used with a graft material that can be placed within the central opening.

In another exemplary embodiment, a method of treating a patient's spine comprises accessing at least a portion of a patient's spine via an oblique angular approach. A spinal implant is then inserted between vertebral bodies of the patient's spine, wherein the spinal implant comprises a body with an upper surface, a lower surface, and a pair of sidewalls extending therebetween. The sidewalls may be connected by an intermediate wall segment and converge at a nose or tip. The pair of sidewalls includes one sidewall that is longer than the other sidewall. The body may further include a central opening extending through the upper and lower surfaces, and one or more apertures within the intermediate wall segment for receiving a fixation element. The spinal implant is introduced into the patient's spine along a trajectory that is at an oblique angle relative to the midline of the spine. The spinal implant may be attached with fixation elements to the vertebral bodies.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 1A-1G show perspective views of an exemplary embodiment of a spinal implant of the present disclosure, in which:

FIG. 1A shows a top-down view of the spinal implant;

FIG. 1B shows a perspective isometric view of the spinal implant of FIG. 1A;

FIG. 1C shows a perspective oblique view of the spinal implant of FIG. 1A;

FIG. 1D shows a rear view of the spinal implant of FIG. 1A;

FIG. 1E shows a side view of the spinal implant of FIG. 1A in use with exemplary bone screws of FIG. 3;

FIG. 1F shows a perspective side view of the spinal implant of FIG. 1A in use with exemplary fixation screws of FIG. 3; and FIG. 1G shows a top-down view of the spinal implant and fixation screws of FIG. 1F.

FIGS. 2A-2B show perspective views of another exemplary embodiment of a spinal implant of the present disclosure, in which:

FIG. 2A illustrates a perspective side view of the spinal implant with exemplary fixation screws of FIG. 3; and FIG. 2B shows a top-down view of the spinal implant and fixation screws of FIG. 2A.

DETAILED DESCRIPTION

The present disclosure provides various spinal implants that are configured for an oblique angular approach into a patient's intervertebral disc space. The spinal implant may be introduced through a narrow access window, while maximizing endplate coverage and promoting sagittal balance. The oblique approach may provide better access to more spinal levels, and may be potentially less invasive compared to midline or lateral approaches.

In accordance with one exemplary embodiment, a spinal implant is provided having an upper surface, a lower surface, a wall at the anterior portion of the implant, two sidewalls connecting the upper and lower surfaces and converging at a nose or tip near the anterior portion of the implant, and one or more apertures within the posterior portion for receiving at least one fixation element, wherein the implant is configured for insertion at an oblique angle into the patient's lumbar spine. The spinal implant may additionally include anti-migration and/or anti-rotation features, visualization markers and fixation element guidance features.

Referring now to FIGS. 1A-1G, an exemplary embodiment of a spinal implant 10 of the present disclosure is shown. The spinal implant 10 may be configured for insertion at an oblique angle into a patient's intervertebral disc space. The spinal implant 10 may be employed in the lumbar region of the spine. However, it is contemplated that the spinal implant 10 may be shaped and sized for use in other areas of the spine as well, such as the thoracic and the cervical region of the spine. Additionally, while the spinal implants 10 of the present disclosure are described as being inserted using an oblique angle approach, it is understood that the spinal implants 10 may also be properly inserted using other techniques as well, including approaches that are not oblique angle approaches. For example, where the shape and geometry of the spinal implant 10 is suited for use in a clinical application but the oblique angle approach is not necessary or desired, then it is understood that the spinal implant 10 may be employed, without restriction to the particular surgical technique to insert the spinal implant 10. In some instances, different spinal levels may require a different insertion approach but would still be able to utilize the spinal implants 10 of the present disclosure. Therefore, the spinal implants 10 may be used at multiple levels, whereby the implants may be inserted at these levels with different approaches.

Figure 1A:
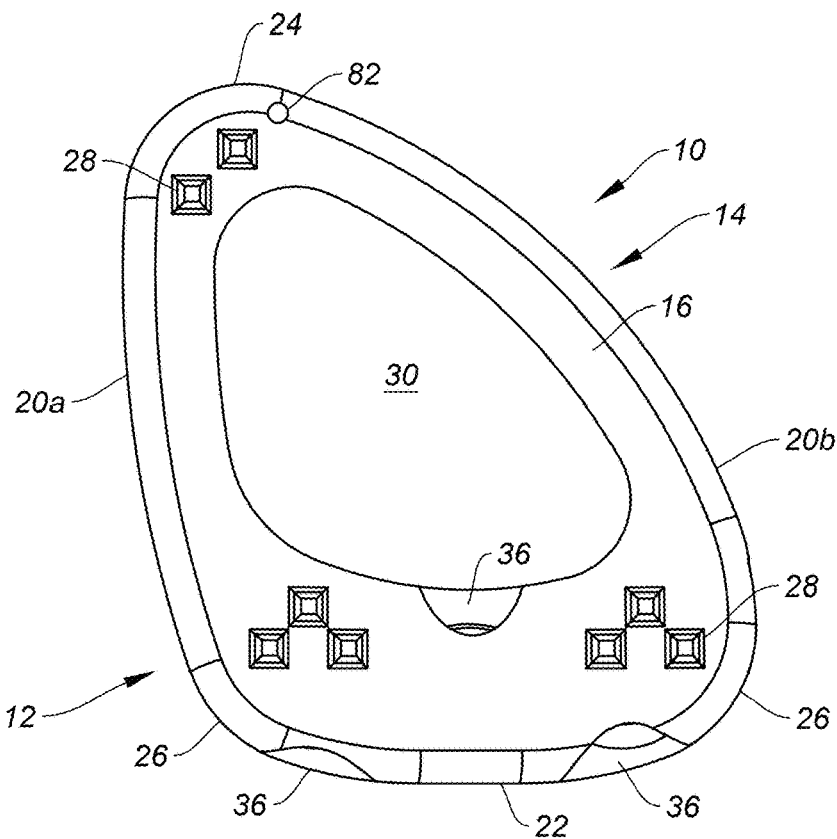

Turning now to the drawings, according to one exemplary embodiment the spinal implant 10 may include anterior and posterior portions 12, 14, and upper and lower surfaces 16, 18 connected by two sidewalls 20a, 20b and intermediate wall 22. The two sidewalls 20a, 20b may converge into a nose or tip 24. This nose or tip 24 may be rounded or tapered. Collectively, the three walls 20a, 20b, 22 may together form a generally triangular profile. However, as shown, one sidewall 20b may be greater in length than the other sidewall 20a, creating a shark's fin-like shape, as best seen in FIG. 1A. Additionally, the walls collectively may also form a rounded or approximately rectangular shape, particularly if one or more of the walls is curved or angled itself.

Figure 1B:
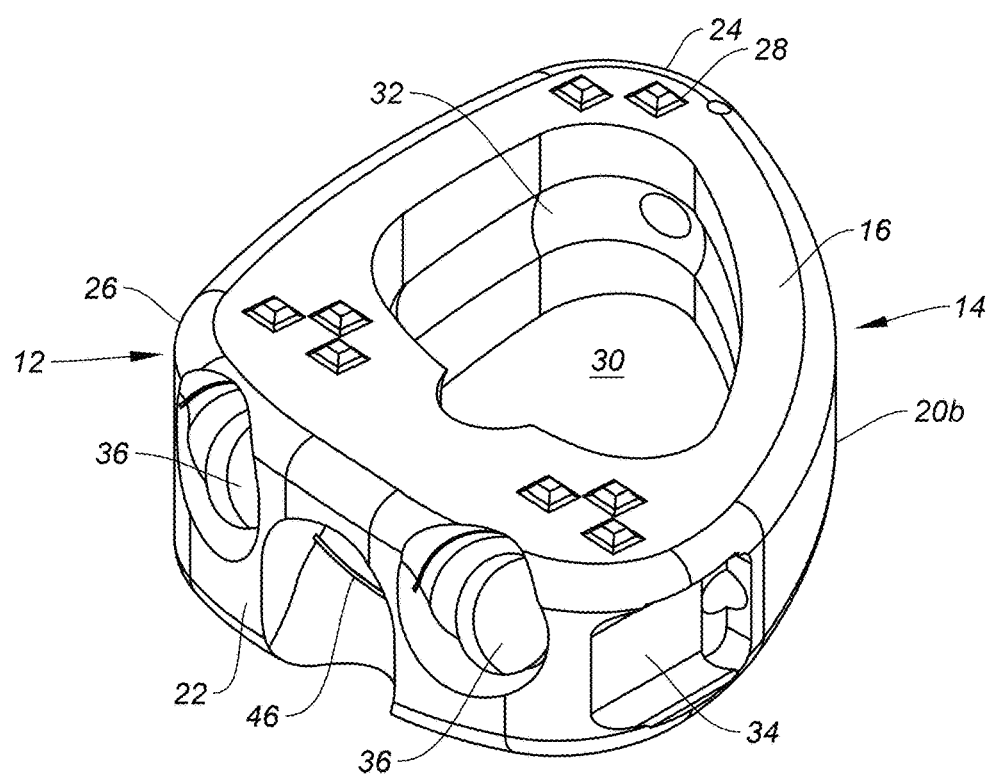
Figure 1C:
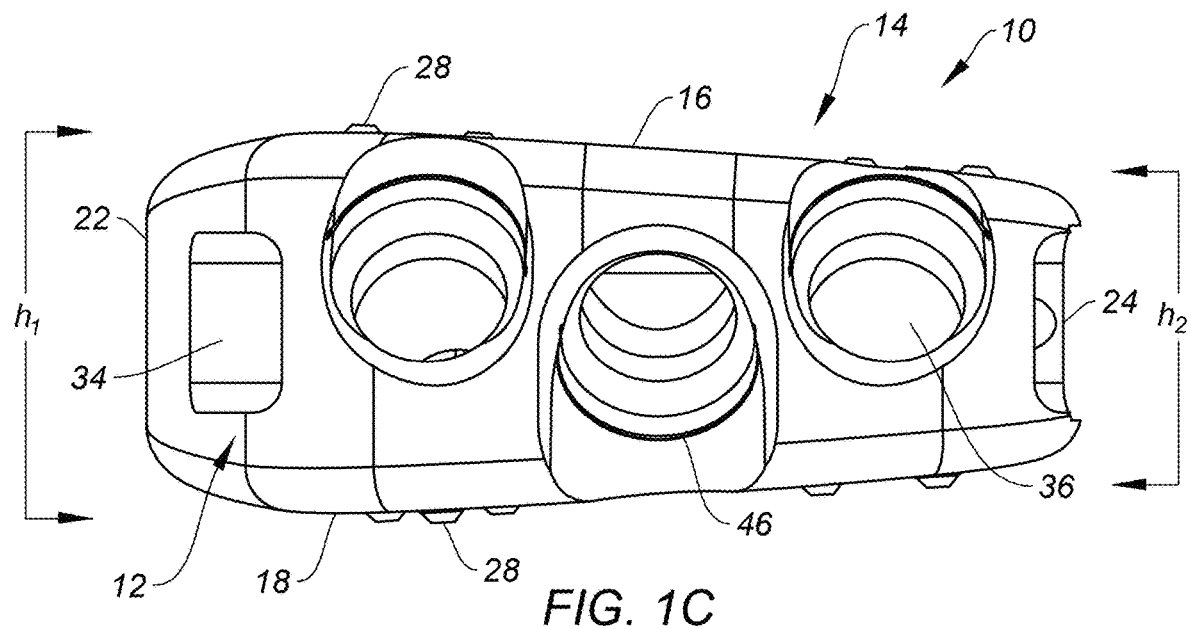
Figure 1D:
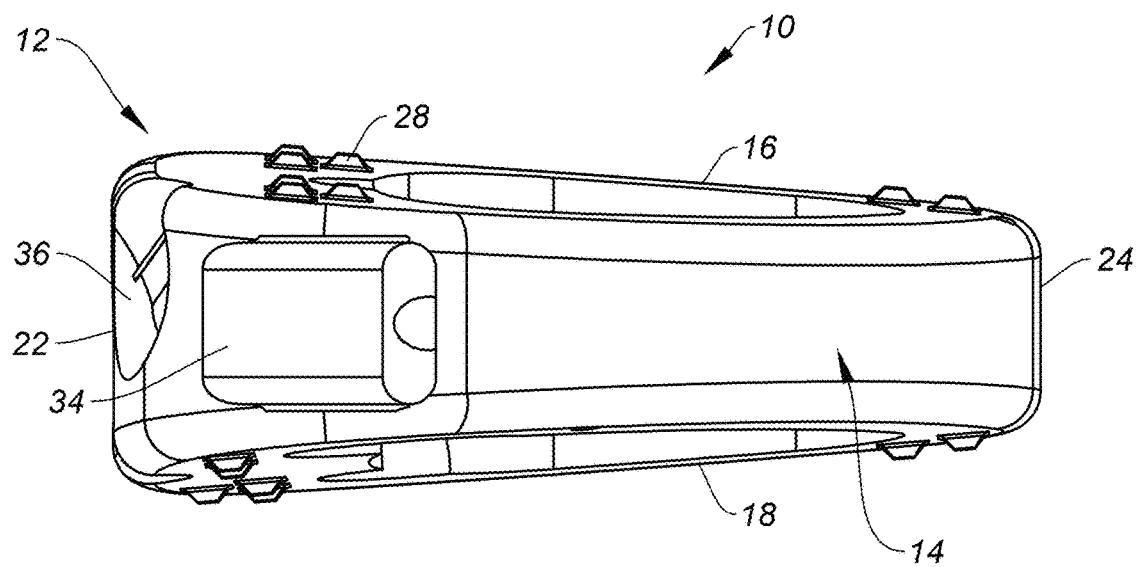

As shown in FIGS. 1C and 1D, the spinal implant 10 may define a generally wedge shaped or anatomically shaped structure, such as a structure having a sharks fin or arrowhead profile, to more closely match the surrounding anatomy of the implant site, for ease of insertion (i.e., to allow tissue distraction), and to be suitable for a tissue sparing or an oblique angular insertion approach. In other words, the height $h_1$ of the anterior portion 12 is greater than the height $h_2$ of the posterior portion 14, the upper and lower surfaces 16, 18 extending along planes that are angled relative to one another to create this tapered appearance. Exemplary heights may be in the range of about 11, 13, and 15 mm, for example. As can be further seen, the implant 10 may have rounded edges, particularly along its outer perimeter. The intermediate wall 22 may extend into convexly curved sidewalls 20a, 20b that intersect at posterolateral corners 26. The posterolateral corners 26 may be rounded, as shown, to provide overall smoothness to the implant profile and prevent undesirable damage to surrounding tissue.

As shown, the spinal implant 10 may include a central opening or lumen 30 extending between the upper and lower surfaces 16, 18 to facilitate bony ingrowth or fusion between adjacent bone segments, such as vertebral bodies. If so desired, the opening 30 may be used as a graft cavity to receive and hold bone graft material, or other biologically active materials like bone cement, bone void filler, bone substitute material, bone chips, demineralized bone matrix, and other similar materials. The spinal implant 10 may be configured in a way that optimizes the opening 30 such that the ratio of the cage or implant structure to the load bearing area is as large as possible. In other words, the implant configuration may allow for a relatively large central opening 30. As shown in FIG. 1B, a graft containment groove 32 may be provided within the opening 30 to contain graft material inside the graft cavity in the center of the implant 10. This groove 32 may be machined along the wall of the cavity 30 to provide additional support in keeping the graft material secured during implantation. Further, the groove 32 may be convex, such as to serve as a boss extending into the central lumen area.

To facilitate attachment of the implant 10 to a tool, such as an insertion tool or other alignment or rotation instruments, instrument guides 34 may be provided on the implant 10 to allow specialized tools to attach to the implant 10. These instrument guides 34, as shown, may be located at or near the anteriorlateral or posterolateral corners 26. The instrument guides 34 may comprise flat surfaces machined into the implant 10 as well as shallow grooves or cutout portions. In some embodiments, these instrument guides 34 may be at a 90 degree to the plane of the screw hole. In other embodiments, the instrument guides 34 may extend parallel or at an angle to the surgical approach.

The upper and lower surfaces 16, 18 may further include surface enhancements 28, such as for example, teeth, ridges, protrusions, ribs, or fins, to enhance bone attachment, prevent migration and generally provide more stability. In one embodiment, the anti-migration and anti-rotation features 28 may comprise pyramid-like protrusions extending from the surface with flattened tops. As further shown, these features 28 may be grouped or clustered in a specific spatial pattern, such as a diagonal pattern. In some embodiments, the surface features 28 may also include a microporous titanium coating on a portion or over the entirety of the features 28. This microporous titanium coating may additionally provide resistance to movement and rotation while fixation elements are being applied to the implant. Of course, it is understood that alternative surface modifications, such as surface roughenings, barbs, spikes, bumps, etc., may also be employed. Further, biological agents, such as bone growth factors may be employed to enhance bone attachment, either alone or in combination with the mechanical enhancements described above.

The spinal implant 10 may include bore or holes 36 to receive fixation elements such as fixation screws 60 therethrough to secure the spinal implant 10 to adjacent bone tissue. In the embodiment shown in FIGS. 1A-1G, the implant 10 may include three holes 36 for receiving three fixation screws 60. The holes 36 may be configured such that one hole 3 is centrally located (i.e., along the center line), and two holes 36 are laterally located (i.e., beside the center line), as illustrated in FIG. 1F. In another embodiment, as shown in FIGS. 2A and 2B, the implant 10 may be configured with two holes 36 to receive two fixation screws 60. Between the two holes 36 an inserter instrument engagement opening 42 may be provided, as shown in FIG. 2A. Accordingly, the present disclosure provides implants 10 having either a three-hole configuration or a two-hole configuration.

In some embodiments, the spinal implant may include other types of fixation mechanisms, including for example, blades or keels. These additional fixation mechanisms may be provided in addition to, or instead of, the fixation elements described above.

Figure 3:
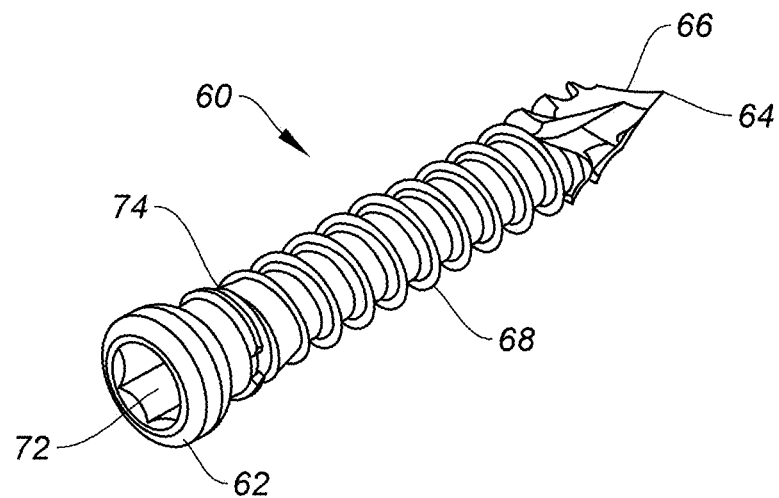
FIG. 3 illustrates a perspective view of an exemplary embodiment of a bone screw of the present disclosure.

FIG. 3 illustrates an exemplary fixation element such as a bone screw 60 that may be used with the implants 10 of the present disclosure. The bone screw 60 may have a head portion 62 and a sharp tip 64 with a threaded shaft 68 extending in between. The sharp tip 64 may comprise a sharp knife edge sufficiently sharp to pierce the vertebral body endplates, preferably without the need for additional instrumentation such as the use of an awl. In one aspect, the screw 60 may be cannulated. In one exemplary embodiment, the threaded shaft 68 may be in the range of about 5.0 mm in diameter, with an inner diameter in the range of about 3.5 mm. The head portion 62 may be a spherically-shaped, shallow screw head having a small radius. The screw head 62 may also include a tool-engaging opening 72, such as a hex socket, for example.

The bone screw 60 may also be used in combination with an anti-backout ring 74. This ring 74 may comprise a compressible split ring that fits into a machined groove 46 in the screw hole 36 to resist screw backout. The bone screw 60 may be provided with an assembled split ring, if so desired. In addition, the screw 60 may include an optional (not shown) visual marker comprising a groove, band, laser etching, or other similar physical indicator that disappears from view when the screw is fully seated, in order to assist with the insertion process. For example, during use, a groove or band laser marked on the screw head 62 otherwise apparent may disappear from view when the screw 60 is fully seated within the screw hole 36 of the implant 10. Thus, the groove or band on the screw head 62 would serve as a visual indicator that the screw 60 has been properly seated within the hole 36. In some embodiments, the screws 60 may comprise cancellous bone screws. Of course, other types of screws 60 may also be employed. Further, as mentioned above, other fixation mechanisms such as keels or blades may also be employed for implant fixation.

According to another aspect of the disclosure, the screws 60 may comprise a porous coating, such as for example, the screws 60 may be plasma spray coated with titanium powder (CPTi). In one embodiment, the threaded shaft portion 68 of the screws 60 may have a porous coating or layer, or may be plasma sprayed. In another embodiment, the screws 60 may be coated with a bone growth enhancing material such as hydroxyapatite (HA) on the threaded shaft portion 68. These treatments allow for added purchase, and may also assist in torque resistance and reduce the instances of screw spinning within the holes 36. The spinal implant 10 itself may also be treated, such as for example, the implant 10 may contain a porous coating or may be plasma spray coated with titanium powder (CPTi) on some or all portions of the implant 10, except the screw holes 36 and inserter groove 34. In some embodiments, the porous plasma spray coating may vary in thickness and porosity. The coating may be located on some or all portions of the body of the spinal implant 10, in order to promote ease of insertion and provide an ideal surface for new bone growth onto the surface.

The screw holes 36 may have a loft geometry surrounding it. Meaning, material may be removed around the screw holes 36 to facilitate screw insertion. Additionally, an indicator groove 46 may be provided on each of the screw holes 36 to facilitate proper screw seating. This indicator groove 46 may be a thin groove that is machined into the screw hole 36 so that it is only visible when the screw 60 is fully seated and the split ring 74 is engaged, for example. In one embodiment, the screw holes 36 may be configured to remain centered relative to the position of the implant 10 as the height increases to allow for one introducer tool to capture the screw holes 36. In another embodiment, the screw holes 36 may be configured to translate with the endplates during use. Other optional visualization assistance features within the screw hole 36 may include etchings, colored bands, or indicator arrows.

Without compromising stability, the lateral holes 36 may be positioned in a manner that avoids the need to retract vessels during surgery. Extended retraction of vessels during surgery may lead to greater chances for complications to the patient. In the embodiments disclosed herein, the lateral holes 36 are positioned so as to provide easier visibility of the surrounding implantation site for the surgeon. In the embodiments shown in FIGS. 1G and 2B, the screw holes 26 are configured such that the screws 60 converge, whether in the three-screw or two-screw configuration. Furthermore, the screw holes 36 may be closely packed and angled so that the screws 60 converge on the oblique line, which is represented by the line B-B offset from the midline A-A in the three-screw configuration illustrated in FIG. 4.

Figure 1E:
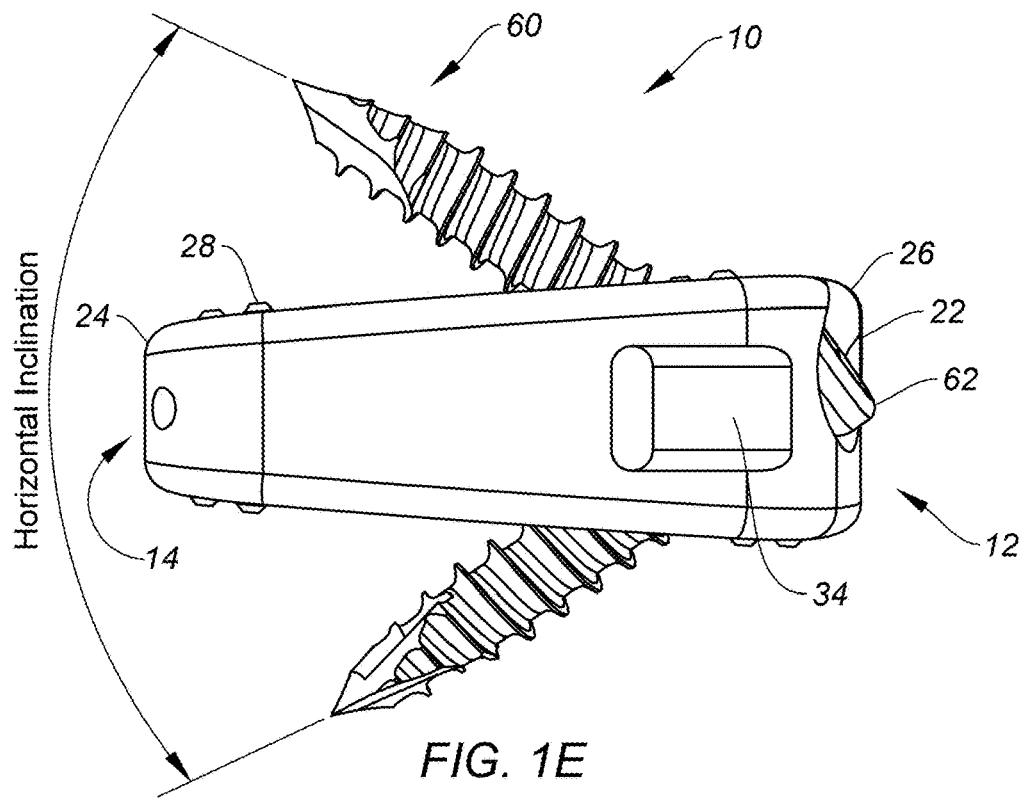
Figure 1F:
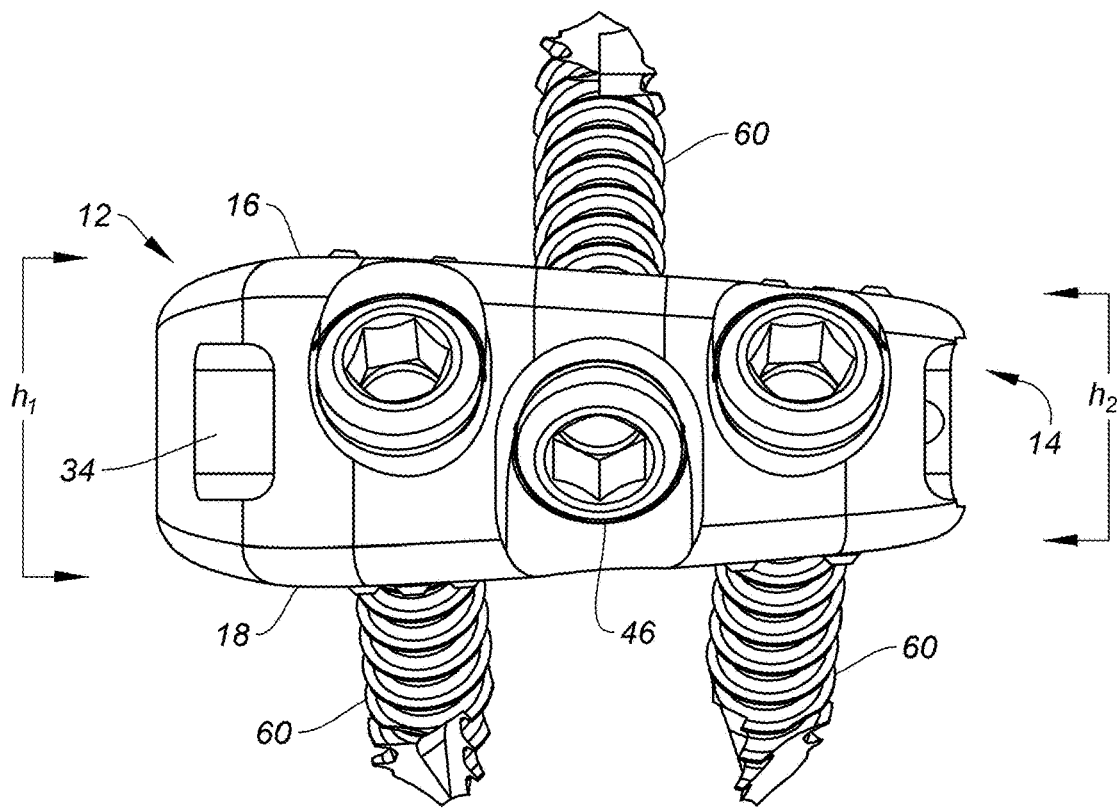
Figure 1G:
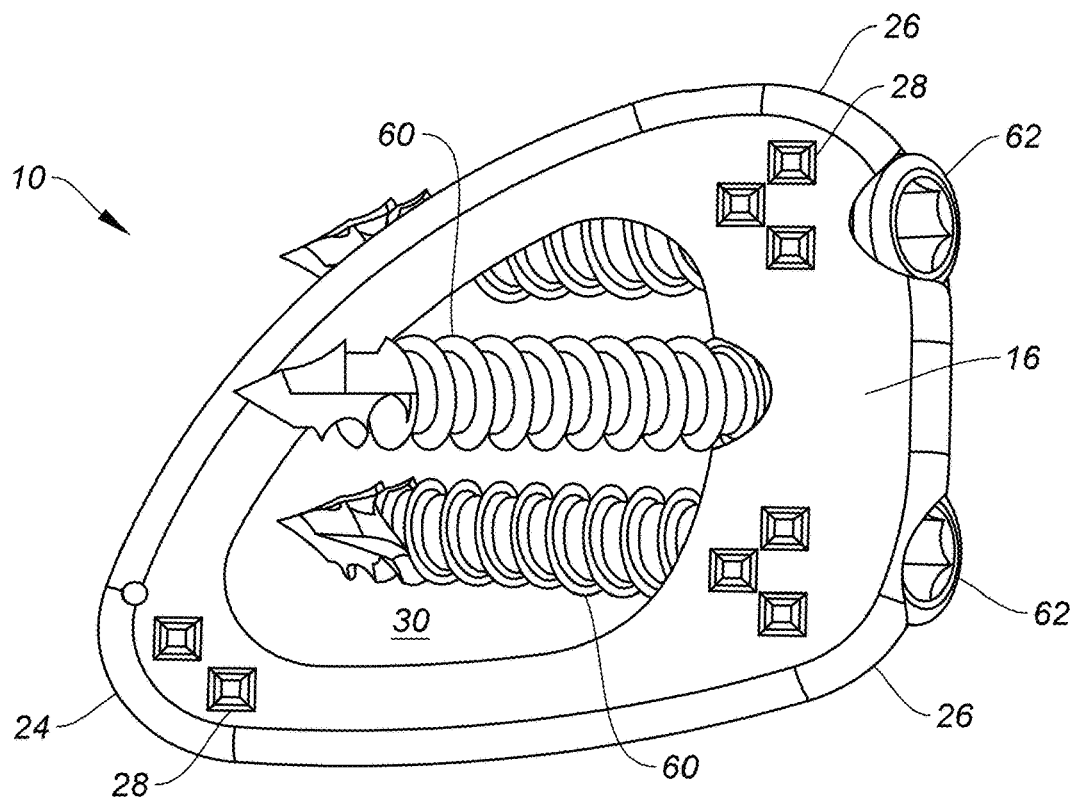
Figure 2A:
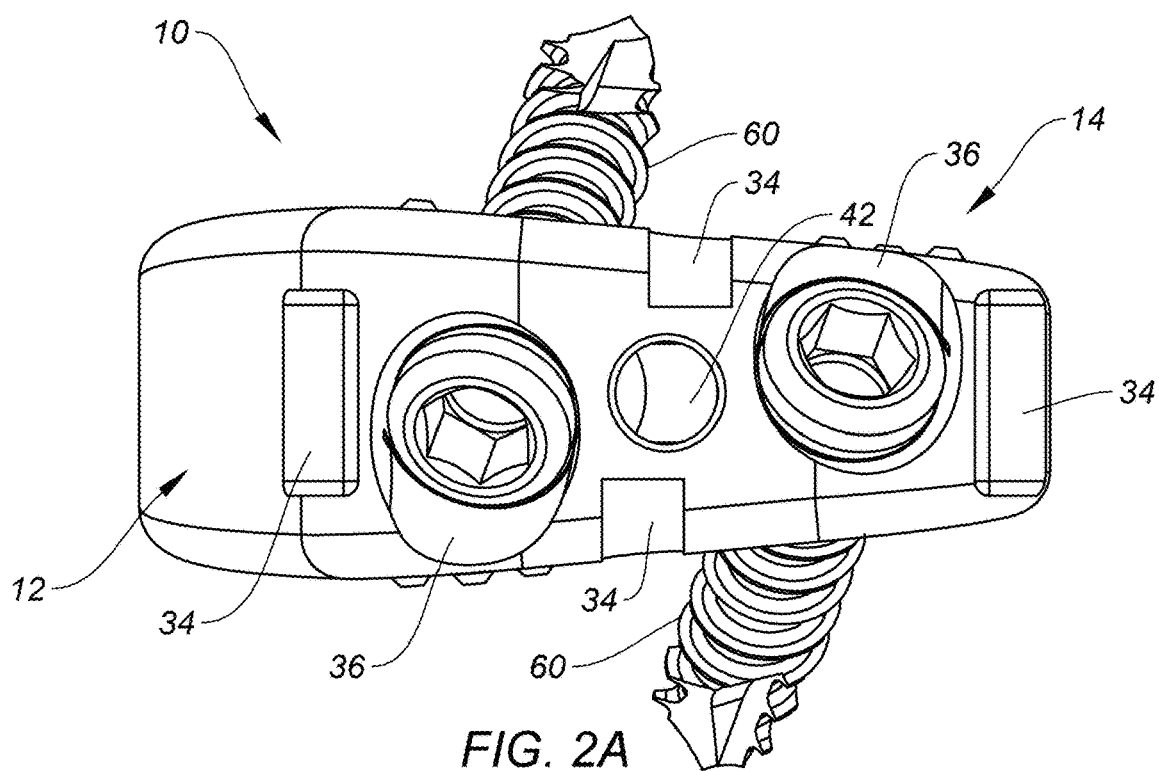
Figure 2B:
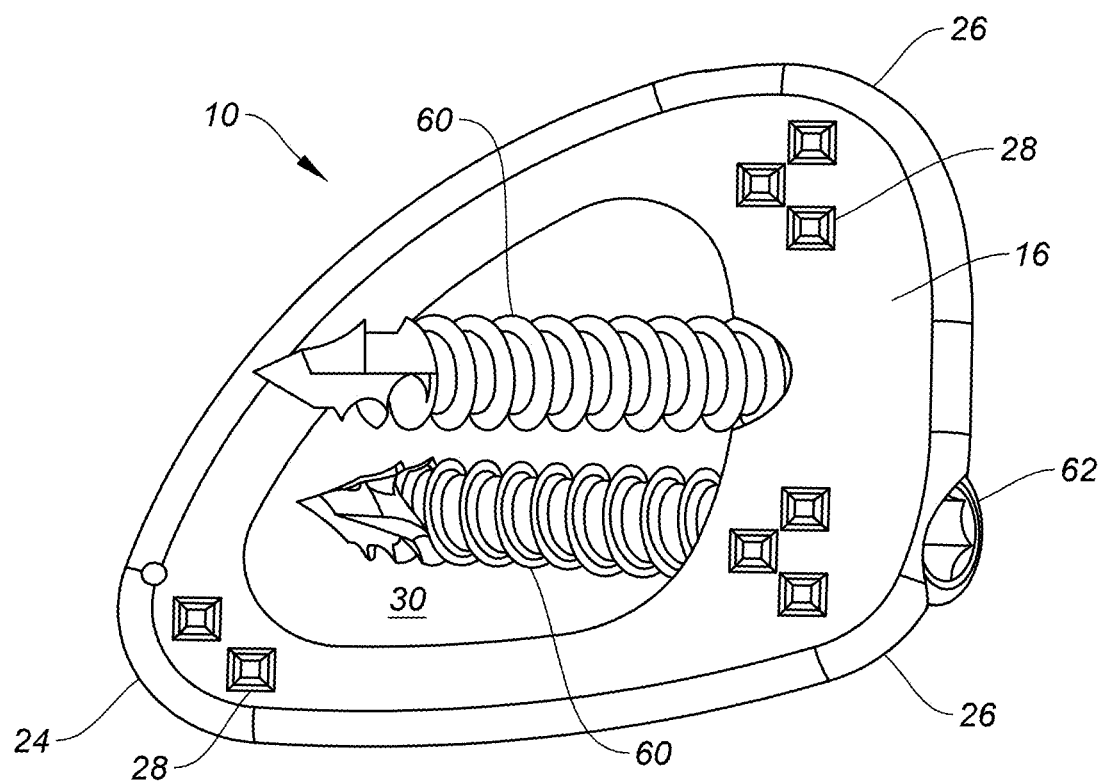

As represented in FIG. 1E, the holes 36 may be configured to allow the screws 60 to have a horizontal inclination in the range of about 35 degrees+/−5 degrees (70 degrees inclusive). Additionally, the positioning of the holes 36 within the spinal implant 10 enable the screws 60 to be closely packed or grouped together for easier access between the anterior vessels 4 and psoas muscle 6. With this configuration, it is contemplated that there would be a restriction on the screw length. Accordingly, in one embodiment the screw lengths may range from about 25 to about 30 mm.

The spinal implant 10 may be provided in a variety of sizes, each of which may comprise a distinct footprint size and may be available in various lodortic angles. As an example, the footprint size of the implant may be within the range of about 26 mm×38 mm up to about 36 mm×48 mm (AP×ML)+/−2 mm. The implant 10 may also be available in lodortic angles of about 8, 12, 14, or 20 degrees, for example. These footprint designs allow the implant 10 to be implanted in the anterior of the vertebral body off the midline by about 40 degrees, or implanted off the lateral by about 20 degrees, for instance, and to accommodate a maximum one inch diameter access window on all sizes, as represented FIG. 4 by line W-W. These access window constraints provide access for fixation screw placement through a window in the range up to about a one inch diameter or 30 mm, while avoiding major vessels 4 and psoas major 6, and would require minimal psoas major retraction and therefore considered minimally invasive. Accordingly, in either the two-screw configuration or three-screw configuration, the spinal implant 10 enables the screws 60 to be positioned within an access window that is no greater than 1 inch in diameter, or 30 mm in width, for minimal disruption of the adjacent anatomy, due to the grouping of the screw holes 36 closely together. In still other embodiments, however, the implant 10 may be implanted at an angle off the midline that ranges anywhere from 0 degrees to 180 degrees, resulting in a completely lateral approach.

The spinal implants of the present disclosure may be provided with internal imaging components to assist in the positioning of the implants and navigation with the instruments. Due to the off-angle insertion approach for these implants 10, visualization becomes critical to proper placement within the spine. Accordingly, the implants 10 may also utilize anti-rotation visualization cues or radiopaque markers 80 for navigation, allowing the surgeon determine if the implant is properly placed by use of lateral x-rays or intraoperative imaging. These imaging components allow the implants to be easily adjusted, such as by rotating, while within the disc space. The adjustment may be made to correct alignment. The imaging components serve as useful navigation tools to otherwise verify proper positioning during the implantation process, as well as to check the position of the implant post-surgery. For instance, the visualization markers may be configured for imaging within the disc space in specific relation to reference planes or anatomical landmarks to enable adjustments to be made to optimize positioning of the spinal implant 10 within the disc space.

Figure 5:
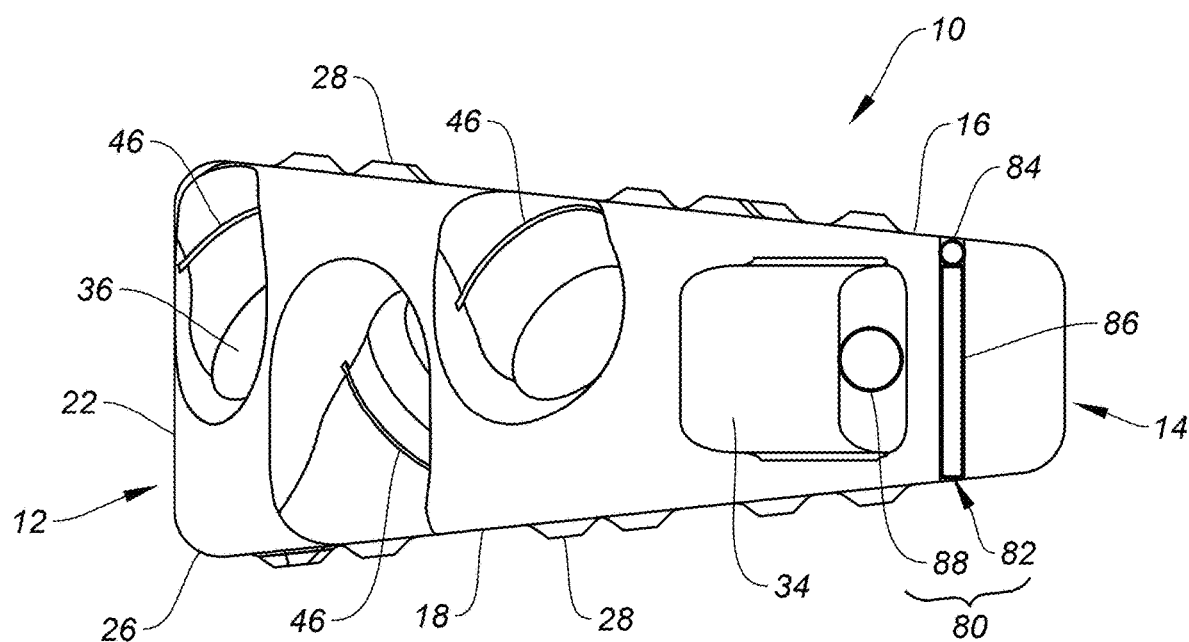
FIG. 5 illustrates a partial cutaway view of the spinal implant of FIG. 1A showing exemplary embodiments of visualization markers of the present disclosure.

In some embodiments, the implants 10 may make use of two radiopaque visualization markers 82, 88. The first marker may comprise an anti-rotation marker 82 that can be used to ensure correct rotational alignment during the implantation process to promote sagittal balance. This anti-rotation marker 82 may comprise a sphere 84 atop a rod or pin 86, as shown in FIG. 5. The rod or pin 86 may be inserted within the implant 10 via small bores (not shown) located at select positions on the implant 10. The marker 82 may comprise, in one example, radiopaque tantalum. In another embodiment, the marker 82 may comprise titanium. During visualization via lateral x-rays or intraoperative imaging, if the implant 10 is rotated, the top of the marker, or sphere 84, will indicate the direction the surgeon should move the implant to realign. In one contemplated application, the sphere 84 can also be used to indicate facet position. Of course, the markers 82, 84, 86 are not limited to the shapes or sizes illustrated, and it is understood that these markers may comprise any size or geometry such as for example, a ring, a sphere, pin or rod, or band, radiopaque coating, a feature, or etching configured to be visualized under radiography.

The second visualization feature may comprise an anti-rotation open ring 88. On lateral x-rays or intraoperative imaging, the ring 88 may be observed as a bright circle. However, if the implant 10 is rotated, an ellipse, or no bright spot or "0" shape, will appear under x-ray visualization or intraoperative imaging. When the implant 10 is correctly aligned, the sphere 84 and rod 86 form an "I" image or constant line, confirming proper rotational position of the implant 10 with respect to the C-arm.

Figure 6:
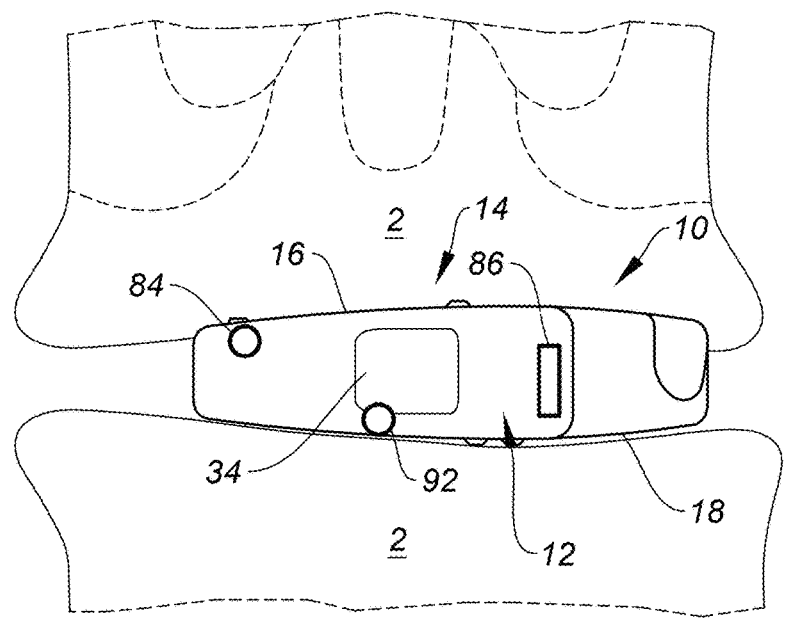
FIG. 6 illustrates a perspective view of the spinal implant of FIG. 1A in situ showing exemplary embodiments of visualization markers of the present disclosure.

These x-ray markers 80 can also be used in A-P (anterior-posterior) x-rays to confirm device position. For instance, as illustrated in FIG. 6, the far marker 84, or posterior marker, may be aligned symmetrically about the mid-plane. This marker 84 may comprise a sphere, ring, pin, band, radiopaque coating, a feature, or etching, or any other suitable shape or geometry configured to be visualized under radiography. Optionally, a midline marker 92 may be provided to indicate spinous process alignment. This midline marker 92, which may be considered an anterior midline marker, may comprise a ring, a sphere, pin or rod, band, radiopaque coating, a feature, or etching, or any other suitable shape or geometry configured to be visualized under radiography.

Alignment verification may be achieved by confirming the position of two of the radiopaque markers relative to one another, and/or in relation to a central of the midline marker 92. For instance, the markers may be aligned to create a continuous straight line to verify that the spinal implant 10 is properly aligned. These markers may also be used to adjust or correct the spinal implant position, in order to maximize the segment angle to be achieved or to achieve a preferred segmental angle of lordosis.

The spinal implant 10 and its components may be formed of any suitable medical grade material, such as biocompatible metals like stainless steel, titanium, titanium alloys, etc. or a medical grade plastic, such as polyetheretherketone (PEEK) or another radiolucent material, ultra high molecular weight polyethylene (UHMWPE), etc. Material stiffness properties along with implant geometry are selected to provide a specific construct stiffness. If so desired, the implant 10 may also be formed of a bioresorbable material. The bioresorbable material may be osteoconductive or osteoinductive, or both.

If desired, the holes 36 of the spinal implant 10 may be configured to permit a predetermined amount of screw toggle (i.e., angular skew) and enable a lag effect when the fixation screw is inserted and resides inside the hole or lumen 36. In other words, the holes 36 may be designed to permit a certain degree of nutation by the screw, and thus, the screws may toggle from one position to one or more different positions, for instance, during subsidence. It also is believed that the predetermined screw toggle (permitted by the clearance between the lumen, or hole 36 and the screw) promotes locking of the screw to the implant 10 after subsidence subsequent to implantation. In one embodiment, the predetermined amount of screw toggle may be in the range of about 3 to 8 degrees, or about 5 to 6 degrees.

Each of the holes 26 may optionally have an opening with a reverse chamfer or overhang feature. This overhang feature would enable the surgeon to better guide the insertion and general approach of the fixation screw 60 into the screw hole 36. Another option may be to provide the openings 36 with a countersink. The countersink feature's center may be offset to the center axis of the hole 36, allowing a countervailing force when the surgeon applies pressure on the fixation screw 60 during insertion, and providing a tactile feedback response to let the surgeon know when the fixation screw's head 62 is properly seated. Thus, the offset would cause the screw head 62 to become loaded (i.e., provide feedback) on final positioning. A portion of the countersink 40 may further optionally have a spherical surface configured to provide a visual feedback response to the surgeon. Of course, the quality and strength of the feedback response also depends on the quality of the bone tissue at the area of treatment. Healthy normal bone tissue will obviously provide the best feedback, as unhealthy, diseased or damaged bone tissue would not have sufficient strength to provide the necessary countervailing force.

Figure 7:
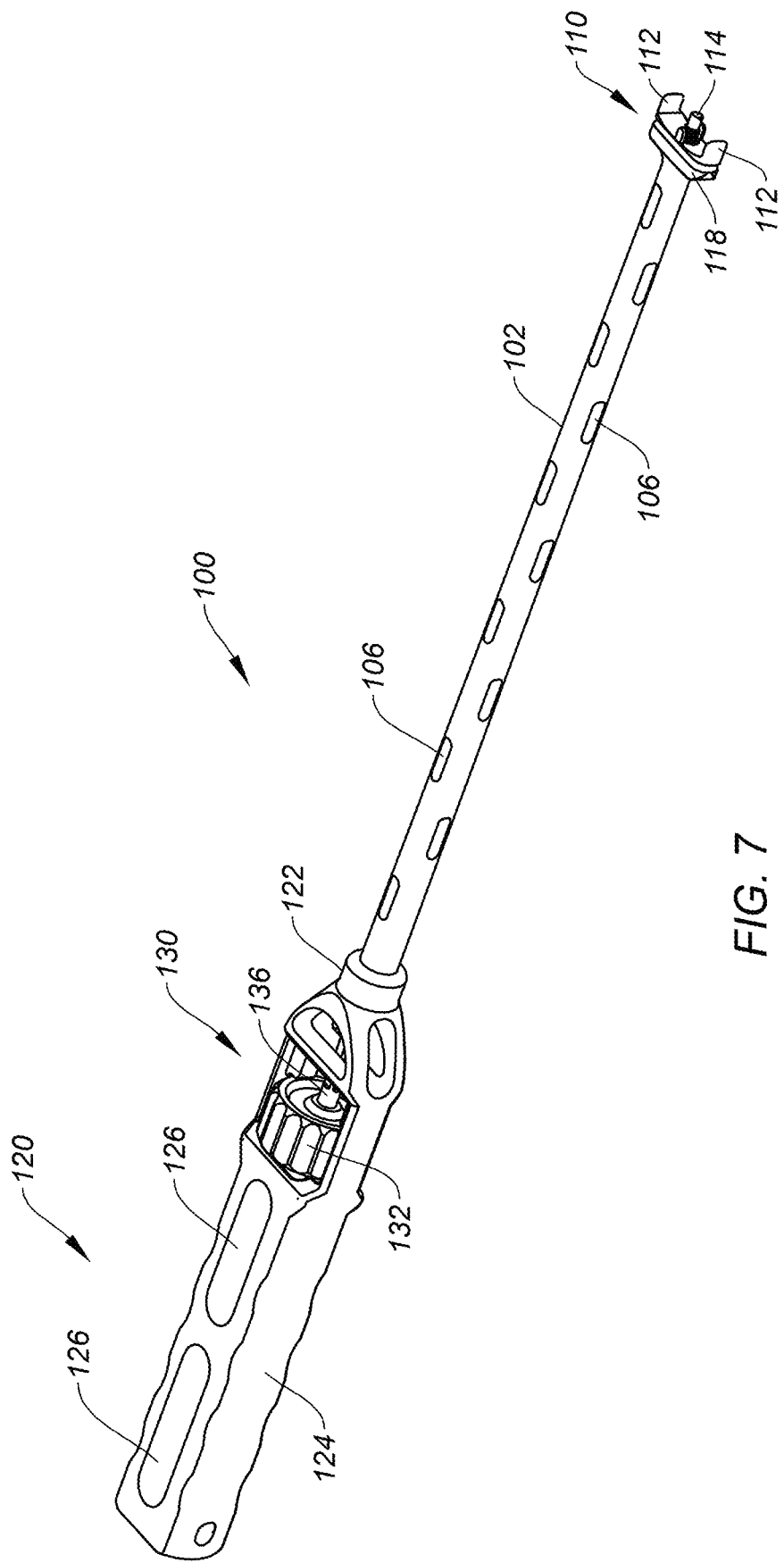
FIG. 7 shows a perspective view of an exemplary embodiment of an insertion tool of the present disclosure.

FIG. 7 represents an exemplary embodiment of an inserter instrument 100 that can be used with the spinal implants 10 of the present disclosure. Inserter instrument 100 may comprise an elongate shaft 102 having spaced apart cleaning slots 106 along its length. The elongate shaft 102 may terminate in a back plate 118 at the working end 110 of the instrument 100. The back plate 118 may be configured to rest against the spinal implant 10, while side bars 112 extending from the back plate 118 may be provided to slide into and securely fit within the instrument guides 34 along the sides of the implant 10. A centrally located insertion pin 114 may be provided to grasp the middle or central screw hole 36 of the three-hole configured implant 10 (see FIG. 8), or the inserter instrument engagement opening 42 in the two-hole configured implant 10. This centrally located insertion pin 114 may cooperate with an actuating shaft 136 housed inside the elongate shaft 102. In some embodiments, this pin 114 may be threaded for engagement with a threaded opening on the implant 10.

Figure 8:
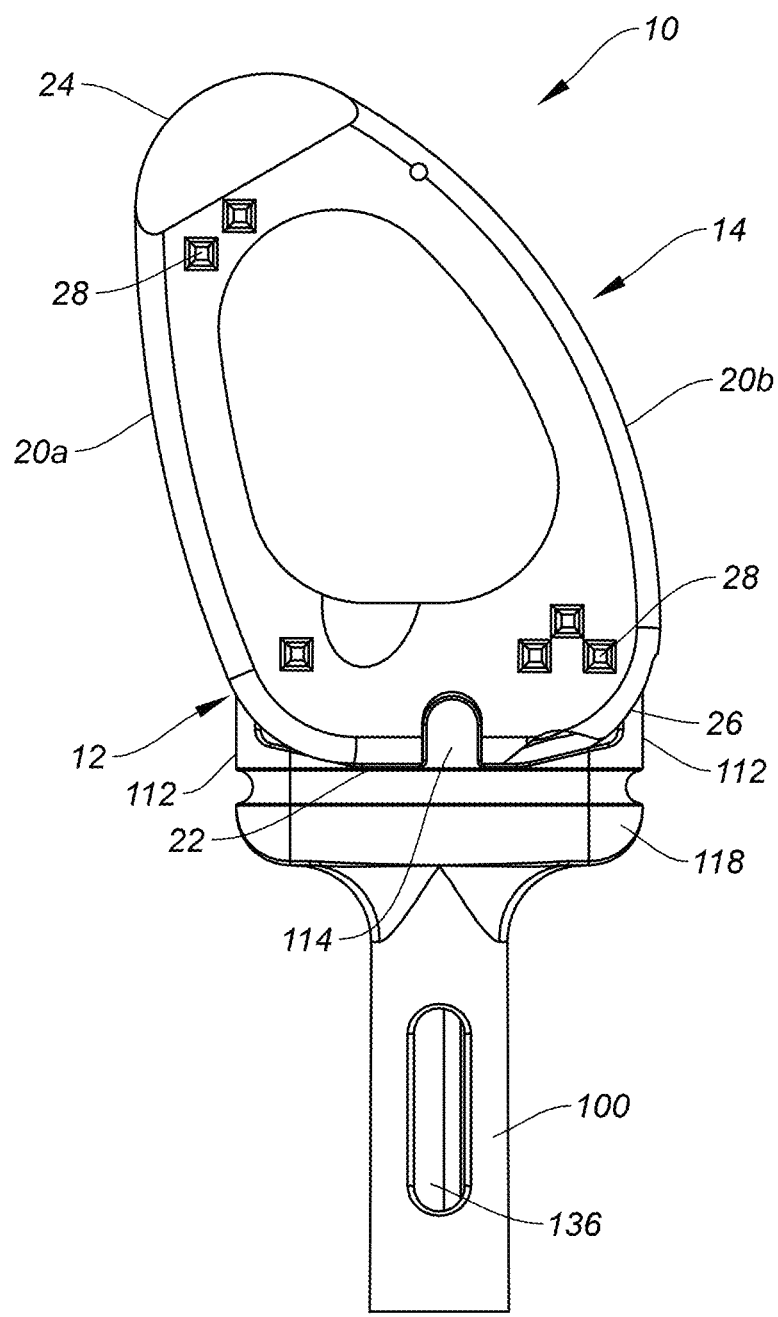
FIG. 8 shows the spinal implant of FIG. 1A in use with the insertion tool of FIG. 7.

As shown, the elongate shaft 102 may be attached to a handle 120 at a neck region 122 of the handle 120. The handle may include a gripping portion 124, and cleaning slots 126. In addition, the handle 120 may include an actuating mechanism 130 to operate the actuating shaft 136. In one embodiment, the actuating mechanism 130 may include a rotating knob 136 that, when rotated, results in the movement of the actuating shaft 136 and consequent translation of the insertion pin 114. In use, the rotating knob 136 may be rotated to allow the insertion pin 114 to engage the middle screw hole 36 of the spinal implant 10 (of the three-hole configuration), as shown in FIG. 8, or the inserter instrument engagement opening 42 of the spinal implant 10 (of the two-hole configuration). When the implant 10 has been properly inserted, the inserter instrument 100 may easily be removed by de-rotating the actuation knob 136, releasing the middle insertion pin 114 from the screw hole 36 or inserter instrument engagement opening 42, and sliding the side bars 112 away from the instrument guides 34.

Figure 4:
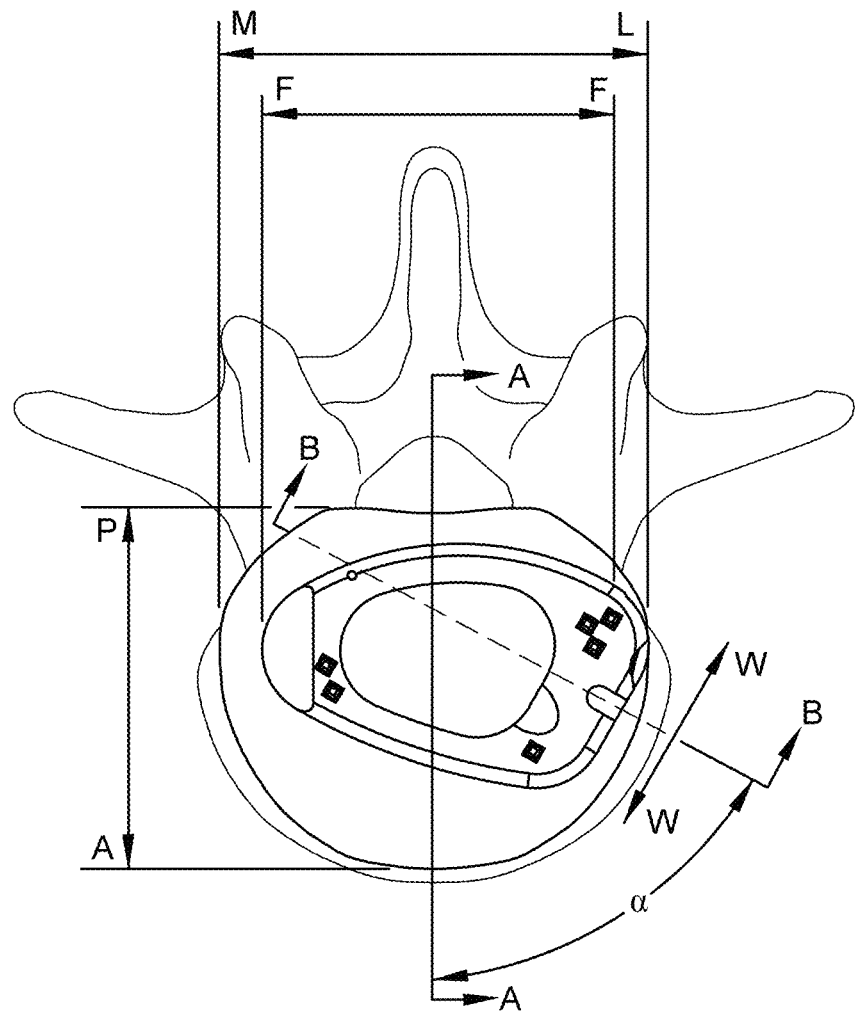
FIG. 4 represents a perspective, top-down view of the spinal implant of FIG. 1A on a vertebral body.

In one exemplary method of inserting the spinal implant 10, an approximately 40 degree from the midline approach is used with the patient in a supine position. In another exemplary method, an approximately 50 degree from the lateral approach is used with the patient in the lateral position. These two approaches reduce contact with psoas 6 and vessels 4. Accordingly, what is meant by an oblique angular approach is an insertion trajectory along an axis represented by the line B-B that is angularly offset from the midline represented by the line A-A by angle α, as represented in FIG. 4, with line A-P representing the anterior-posterior direction, line M-L representing the medial-lateral direction, and line F-F representing the distance between facets.

First, in order to set the approach angle, A-P and lateral x-rays may be taken of the spine. From the vertical axis, under fluoroscopy, the C-arm may be rotated by the appropriate degree (i.e., 40 or 50 degrees) based on the type of approach taken, as previously mentioned. Of course, the C-arm may also be rotated by other angles, such as for example, from a range of 0 degrees off the midline to about 90 degrees from the midline.

Next, an incision may be created and the user may approach the spine in line with the previously determined C-arm angle from the prior step, via a retroperitoneal approach. A dilator may be used to confirm disc location, with a bias to the psoas, and a K-wire may be placed through the dilator. The dilator can then be replaced with a slide instrument. Retractor blades can then be inserted to retract psoas 6 to create an access window approximately 30 mm wide, or about 1 inches in diameter, or smaller. Vasculature should be avoided during the process.

Then, the surgeon may prepare the implantation site by removing some disc material from the disc space (i.e., diskecktomy) using available instrumentation. The spinal implant 10 may be provided to the surgeon with the screws pre-attached, or separately, as desired. Once the implant 10 is loaded onto an inserter instrument 100, such as the one shown in FIG. 7, the implant 10 may be aligned with the center screw hole 36 angled superiorly. The surgeon then introduces the implant 10 under fluoroscopy.

Following insertion, the surgeon visualizes and verifies proper implant positioning. If the sphere marker 84 of the implant 10 is posterior, the surgeon would move the inserter instrument 100 posterior or closer to the C-arm of the fluoroscope so 'I' the marker 86 and sphere marker 84 form a single constant line (or close to it). If the sphere marker 84 is anterior, then the surgeon would move the inserter instrument 100 anterior or away from the C-arm.

Figure 9:
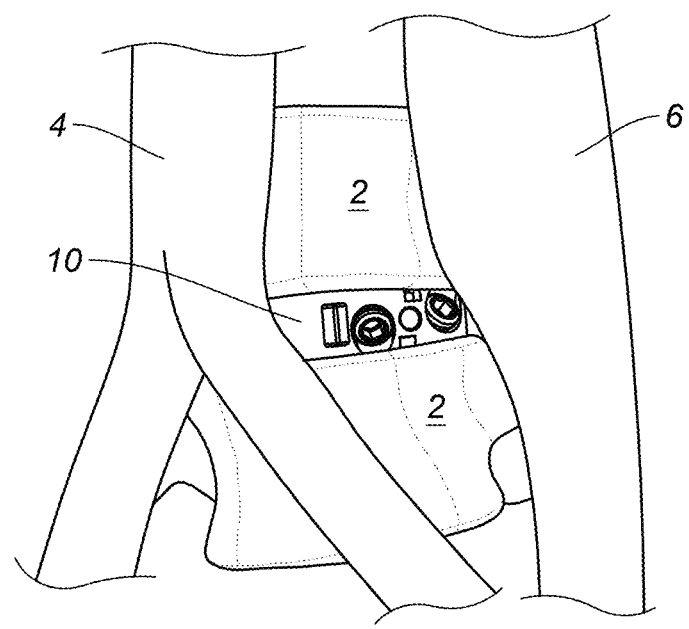
FIG. 9 represents a perspective view of the spinal implant of FIG. 1A in situ.

Starting with the center screw hole 36, the surgeon can now insert the bone screw 60 into the center hole 36 first, in a three-screw configuration, and then follow with insertion of the other bone screws 60 in the other holes 36 lateral to the center hole. Finally, A-P and lateral x-rays may be taken to confirm the final implant position. Screw insertion may be accomplished via a very narrow access, with an access window no greater than about 30 mm or 1 inch in diameter as mentioned above, for a three-screw configuration (the window could be even smaller for a two-screw configuration). Accordingly, this entire process may be accomplished as an open or a minimally invasive procedure, maximizing endplate coverage and promoting sagittal balance. The oblique approach described herein provides better access to more spinal levels and is potentially less invasive than midline or lateral approaches. As illustrated in FIG. 9, in situ, the spinal implant 10 may be fully inserted while avoiding any disruption of the anterior vessels 4 or psoas major 6 during insertion by this approach.

Where toggling is desired, the implant 10 may be configured to permit a predetermined amount of screw toggle and enable a lag effect when the fixation screw is inserted and resides inside the screw hole 36. Upon tightening, the lag effect may be observed whereby the implant 10 draws bone tissue towards itself, which may promote better fusion. Since the screws do not completely lock due to the lag effect, no screw backout occurs.

It will also be appreciated that the angular positioning of the various holes, as described above, allows the present implant 10 to be of a relatively small size and therefore insertable from an oblique angular approach into the intervertebral spaces of the spine. Thus, it will be appreciated that the angular positioning of the holes can assist effective operation of the implant 10 and the ability to "stack" implants in adjacent multilevel procedures without the securing means interfering with each other. Such a feature can be of major significance in some situations and applications.

Although the following discussion focuses on spinal implants or prostheses, it will be appreciated that many of the principles may equally be applied to other structural body parts within a human or animal body.

Other embodiments of the disclosure will be apparent to those skilled in the art from consideration of the specification and practice of the disclosure provided herein. It is intended that the specification and examples be considered as exemplary only.

What is claimed is:

1. A method of treating a patient's spine, comprising:
    accessing at least a portion of a patient's spine;
    inserting a spinal implant between vertebral bodies of the patient's spine, wherein the spinal implant comprises: a body having an upper surface, a lower surface, and a pair of sidewalls extending therebetween, the sidewalls being connected by an intermediate wall segment at a corner and converging with each other at a rounded nose to form three sides with a substantially triangular profile, the pair of sidewalls including one sidewall that is longer than the other sidewall, the body further including a central opening extending through the upper and lower surfaces, and two or more apertures within the intermediate wall segment for receiving a fixation element; and
    wherein the spinal implant is introduced into the patient's spine along an axis of trajectory that is at an oblique angle relative to the midline of the spine.

2. The method of claim 1, wherein the spinal implant includes visualization markers, and further including the step of positioning the implant by observing the visualization markers under x-ray or intraoperative imaging.

3. The method of claim 1, wherein at least one of the visualization markers is a radiopaque anti-rotation marker, and further including the step of verifying alignment of the spinal implant by confirming the correct position of two of the visualization markers relative to one another.

4. The method of claim 3, wherein the step of verifying alignment of the spinal implant comprises aligning two visualization markers to create a continuous straight line.

5. The method of claim 3, further including the step of securing the spinal implant with fixation elements after proper implant position has been verified.

6. The method of claim 1, wherein the spinal implant includes visualization markers, and further including the step of adjusting the implant position by observing the visualization markers until a maximum segment angle is achieved.

7. The method of claim 1, wherein the spinal implant includes visualization markers, and further including the step of adjusting the implant position by observing the visualization markers until a preferred segmental angle of lordosis is achieved.

8. The method of claim 1, wherein the body has a generally wedge shape.

9. The method of claim 1, wherein the body comprises a posterior portion and an anterior portion, the anterior portion having a greater height than the posterior portion in a direction substantially perpendicular to the upper and lower surfaces.

10. A method of treating a patient's spine, comprising:
    accessing at least a portion of a patient's spine; and
    introducing a spinal implant along an axis of trajectory that is at an oblique angle
    relative to the midline of the spine between vertebral bodies of the patient's spine, wherein the spinal implant comprises: a body having an upper surface, a lower surface, and a pair of sidewalls extending therebetween, the sidewalls being connected by an intermediate wall segment and converging with each other at a rounded nose to form a substantially triangular profile, the pair of sidewalls including one sidewall that is longer than the other sidewall, the body further including a central opening extending through the upper and lower surfaces, and two or more apertures within the intermediate wall segment for receiving a fixation element.

11. The method of claim 10, wherein the spinal implant includes visualization markers, and further including the step of positioning the implant by observing the visualization markers under x-ray or intraoperative imaging.

12. The method of claim 10, wherein at least one of the visualization markers is a radiopaque anti-rotation marker, and further including the step of verifying alignment of the spinal implant by confirming the correct position of two of the visualization markers relative to one another.

13. The method of claim 12, wherein the step of verifying alignment of the spinal implant comprises aligning two visualization markers to create a continuous straight line.

14. The method of claim 12, further including the step of securing the spinal implant with fixation elements after proper implant position has been verified.

15. The method of claim 10, wherein the spinal implant includes visualization markers, and further including the step of adjusting the implant position by observing the visualization markers until a maximum segment angle is achieved.

16. The method of claim 10, wherein the spinal implant includes visualization markers, and further including the step of adjusting the implant position by observing the visualization markers until a preferred segmental angle of lordosis is achieved.

17. The method of claim 10, wherein the body comprises a posterior portion and an anterior portion, the anterior portion having a greater height than the posterior portion in a direction substantially perpendicular to the upper and lower surfaces.

18. A method of treating a patient's spine, comprising:
accessing at least a portion of a patient's spine; and
introducing a spinal implant along an axis of trajectory that is at an oblique angle
relative to the midline of the spine between vertebral bodies of the patient's spine, wherein the spinal implant comprises: a body having an upper surface, a lower surface, and a pair of sidewalls extending therebetween, the sidewalls being connected by an intermediate wall segment to form a shark's fin-like shape, the pair of sidewalls including one sidewall that is longer than the other sidewall, the body further including a central opening extending through the upper and lower surfaces, and two or more apertures within the intermediate wall segment for receiving a fixation element.

19. The method of claim 18, wherein pair of sidewalls converge with each other at a rounded nose to form three sides with a substantially triangular profile.

* * * * *